US008597388B2

(12) United States Patent
Schaaf et al.

(10) Patent No.: US 8,597,388 B2
(45) Date of Patent: Dec. 3, 2013

(54) SYSTEM FOR MAKING A DENTAL RESTORATION PROVIDING VENTILATION OF A CONTROL UNIT OF THE SYSTEM, AND A CORRESPONDING METHOD

(75) Inventors: Michael K. Schaaf, Herrsching (DE); Christian A. Richter, Feldafing (DE); Sebastian Guggenmos, Peissenberg (DE); Günter Hertlein, Seefeld (DE); Erich Sendelbach, Peissenberg (DE)

(73) Assignee: 3M Innovative Properties Company, St. Paul, MN (US)

( * ) Notice: Subject to any disclaimer, the term of this patent is extended or adjusted under 35 U.S.C. 154(b) by 2 days.

(21) Appl. No.: 13/127,086

(22) PCT Filed: Oct. 14, 2009

(86) PCT No.: PCT/US2009/060575
§ 371 (c)(1),
(2), (4) Date: Jul. 25, 2011

(87) PCT Pub. No.: WO2010/051159
PCT Pub. Date: May 6, 2010

(65) Prior Publication Data
US 2011/0272837 A1    Nov. 10, 2011

(30) Foreign Application Priority Data
Nov. 3, 2008   (GB) .................................. 0820018.0

(51) Int. Cl.
*B01F 11/00* (2006.01)
(52) U.S. Cl.
USPC ............ 55/385.1; 433/114; 433/148; 451/56; 451/57; 451/58

(58) Field of Classification Search
USPC ........ 55/340, 410, 417, 467, 473, 485, 385.1; 95/8, 90, 287, 900; 366/139, 602; 433/114, 148; 451/56, 57, 58
See application file for complete search history.

(56) References Cited

U.S. PATENT DOCUMENTS 1,796,470 A    3/1931   Meyer
1,899,718 A    2/1933   Poston
(Continued)

FOREIGN PATENT DOCUMENTS

DE    2944397    5/1981
DE    3226100    1/1984
(Continued)

OTHER PUBLICATIONS

Search Report for GB0820018, dated Feb. 5, 2009, 4 pages.
(Continued)

*Primary Examiner* — Duane Smith
*Assistant Examiner* — Minh-Chau Pham
(74) *Attorney, Agent, or Firm* — X. Christina Huang

(57) ABSTRACT

In one embodiment, a system for making a dental restoration is provided. The system includes a machine unit for processing a dental material to form the dental restoration, and a control unit for controlling the operation of the machine unit. An air channel for discharging a process-originated material from the machine unit provides an air connection between the machine unit and the control unit. Certain embodiments of invention are advantageous in that they help to increase the reliability of the machining operation.

15 Claims, 2 Drawing Sheets

(56) References Cited

U.S. PATENT DOCUMENTS

| | | | |
|---|---|---|---|
| 2,355,853 A | 8/1944 | Foxon | |
| 2,409,783 A | 10/1946 | Moskey | |
| 3,276,122 A | 10/1966 | Slayton | |
| 4,047,913 A * | 9/1977 | Okumura | 55/418 |
| 4,226,054 A * | 10/1980 | Coty | 451/453 |
| 4,252,054 A * | 2/1981 | Bakels | 433/92 |
| 4,546,261 A | 10/1985 | Gonser | |
| 4,582,998 A | 4/1986 | Gonser | |
| 5,033,238 A | 7/1991 | Zubler | |
| 5,336,128 A * | 8/1994 | Birdsong | 454/56 |
| 5,383,752 A | 1/1995 | Rheinberger | |
| 5,423,779 A * | 6/1995 | Yeh | 604/317 |
| 5,490,810 A | 2/1996 | Hahn | |
| 5,939,211 A | 8/1999 | Mörmann | |
| 6,224,371 B1 | 5/2001 | De Luca | |
| 6,454,568 B1 | 9/2002 | Beuschel | |
| 6,769,912 B2 | 8/2004 | Beuschel | |
| 6,905,293 B1 | 6/2005 | Filser | |
| 7,150,778 B1 * | 12/2006 | Dauber et al. | 95/8 |
| 7,635,401 B2 * | 12/2009 | Dietz | 55/385.1 |
| D627,472 S | 11/2010 | Wagner | |
| D627,473 S | 11/2010 | Wagner | |
| D627,889 S | 11/2010 | Wagner | |
| 8,251,254 B2 | 8/2012 | Guggenmos | |
| 2001/0055238 A1 * | 12/2001 | Suzuki et al. | 366/139 |
| 2004/0031248 A1 * | 2/2004 | Lindsay | 55/385.3 |
| 2008/0089966 A1 * | 4/2008 | Wachter et al. | 425/175 |
| 2008/0307970 A1 * | 12/2008 | Augustine et al. | 95/273 |
| 2009/0031684 A1 * | 2/2009 | Ragona | 55/383 |
| 2010/0000677 A1 | 1/2010 | Guggenmos | |
| 2010/0209876 A1 | 8/2010 | Wagner | |
| 2011/0108143 A1 * | 5/2011 | Caluori | 137/561 R |
| 2011/0236860 A1 | 9/2011 | Jahns | |

FOREIGN PATENT DOCUMENTS

| | | |
|---|---|---|
| DE | 3829817 | 3/1990 |
| DE | 4325608 | 2/1995 |
| DE | 19734628 | 2/1999 |
| EP | 455854 | 11/1991 |
| EP | 1195226 | 4/2002 |
| EP | 1878404 | 1/2008 |
| JP | 8173459 | 7/1996 |
| JP | 8280716 | 10/1996 |
| JP | 2008-061982 | 3/2008 |
| WO | 95-30382 | 11/1995 |
| WO | 02-076328 | 10/2002 |
| WO | 2007-141523 | 12/2007 |
| WO | 2008-097874 | 8/2008 |
| WO | 2010-051159 | 5/2010 |
| WO | 2010-062672 | 6/2010 |

OTHER PUBLICATIONS

International Search Report for PCT/US2009/060575, Mailed Jan. 19, 2010, 4 pages.
Search Report for GB0820017.2, Dated Feb. 5, 2009, 4 pages.
International Search Report for PCT/US2009-062706, Mailed Jan. 1, 2010, 4 pages.
Search Report for EP 99 11 6985.5, Dated Mar. 7, 2002, 3 pages.

* cited by examiner

SYSTEM FOR MAKING A DENTAL RESTORATION PROVIDING VENTILATION OF A CONTROL UNIT OF THE SYSTEM, AND A CORRESPONDING METHOD

CROSS REFERENCE TO RELATED APPLICATIONS

This application is a national stage filing under 35 U.S.C. 371 of PCT/US2009/060575, filed Oct. 14, 2009, which claims priority to GB Application No. 0820018.0, filed Nov. 3, 2008, the disclosure of which is incorporated by reference in its/their entirety herein.

FIELD OF THE INVENTION

The invention relates to a system for making a dental restoration, comprising a machine unit and a control unit that are interconnected by an air connection for ventilating the control unit. The invention further relates to a method of ventilating a control unit of a system for making a dental restoration.

BACKGROUND OF THE INVENTION

Dental restorations or prostheses are often manufactured by use of automated processes. In such automated processes ceramic and/or glass-ceramic materials are often used which also allow for making high-quality dental restorations because of their good physical, aesthetic and biological properties. Typically the manufacturing process for such restorations includes the steps of capturing data representing the shape of a patient's teeth, designing at least part of the dental restoration based on the captured data using computer-aided design (CAD) software, and manufacturing the dental restoration on an automated Computer Numerical Controlled (CNC) machine. An exemplary CNC machine for making dental restorations is available from 3M ESPE AG (Seefeld, Germany) under the trade designation LAVA™ Form Milling Unit.

Machines of this type are designed to automatically machine a dental restoration, parts of a dental restoration or precursors of such. In particular for machines that produce dental restorations from blanks by removing material, for example by milling or grinding, it is desirable that the removed material is, preferably continuously, discharged from the machine to avoid interruptions of the manufacturing for disposing accumulated material. In case of machining ceramic or glass-ceramic material the removed material is also often present in the form of small particles or dust which may be generally undesirable in a manufacturing process because small particles or dust may cause wear on machine parts or contaminate the environment.

Although current machines may provide a variety of advantages, there is still a need for a device and a process which provide maximum reliability and require minimal maintenance efforts. Further such device and process are desirably inexpensive, and provide high quality dental restorations.

SUMMARY OF THE INVENTION

A first aspect of the invention is directed to a system for making a dental workpiece. The system comprises a machine unit for processing a dental material to form the dental workpiece, a control unit for controlling the operation of the machine unit, and an air connection between the machine unit and the control unit. The system is further adapted to generate a flow of air for entraining the process-originated material in the air, and to discharge the process-originated material entrained in the air through the air connection.

The term "dental workpiece" as it is used within this specification generally refers to a dental restoration, a precursor of a dental restoration, or a blank of a dental material for making a dental restoration or a precursor thereof.

The term "entrain" for the purpose of this invention refers to causing movement of a particle by a fluid flow.

The term "process-originated material" may include particles of the workpiece itself, particles of a coating on the workpiece, processing aids (liquid or solid lubricants, for example), or parts of the machining tool, for example, or any other particles or gases that emerge from processing the dental workpiece.

As an advantage of the present invention a device may be provided which ventilates the control unit with filtered air. Penetration of unwanted particles into the control unit, and particularly into the electronic circuitry in the control unit, may thereby be prevented. The electronic circuitry of the control unit may further be kept at a desired temperature during operation of the system, or at least below a particular maximum temperature. In particular reliable cooling of the electronic circuitry may be achieved. The present invention further provides the advantage that separate filters and ventilation sub-systems used exclusively for ventilating the control unit are unnecessary. Further a system of the invention may be operated even in a dusty environment, because air from the environment may be guided through an effective filter before the air is used for ventilating the control unit. The system may also provide for cleaning the air in the environment when in operation, for example when used in a dental lab. As another advantage preferably only one or a minimal number of filters may require maintenance or need to be exchanged from time to time. It is also an advantage of the present invention that a single standard ventilation device, such as a suction unit, may be used both to discharge process-originated material, and to ventilate or cool the control unit.

In one embodiment an air channel provides the air connection between the machine unit and the control unit. Such an air channel may be a pipe, a hose, an opening or any other suitable structure adapted for providing an air connection between two locations.

In another embodiment the system of the invention is adapted to machine the dental material, for example a dental ceramic or dental glass-ceramic material. The system may particularly be adapted to mill or grind the dental material. The process-originated material may for example correspond to material removed in a machining process to shape the dental workpiece. In particular, the process-originated material may comprise (or be generally in the form of) particles of the dental material, for example chips and/or dust. The process-originated material may for example be sucked away from the machine unit by the air, and the same air may then be guided through the air connection towards or into the control unit.

In one embodiment the air connection has an inlet connected with the machine unit for receiving air from the machine unit and an outlet connected with the control unit for emitting the air towards the control unit. The inlet is preferably also arranged relative to the machine unit and adapted to receive the process-originated material that may be entrained in the air. The inlet may for example be funnel shaped with the funnel opening away from an air channel.

In a further embodiment the system is connectable or connected to a ventilation device which is adapted to generate an air flow in the air connection, such that the air connection receives the air in the inlet and emits the air from the outlet. Therefore the ventilation device is preferably adapted to generate an air flow in the air connection, such that the air connection receives the air from the machine unit and emits the air towards the control unit.

In one embodiment the air connection provides the air connection between a machining chamber of the machine unit and the control unit. The machining chamber preferably contains or accommodates the process, for example houses the site where the workpiece is processed. The machining chamber may have a cabinet with an openable door. The door may allow a user to access the inside of the chamber, for example for maintenance work or troubleshooting. In the machining chamber a support for positioning the dental workpiece may be arranged. Sliding or other positioning mechanisms may be arranged within the machining chamber for moving the dental workpiece and a machining tool relative to one another. Preferably such slides are adapted and arranged with respect one another such that the dental workpiece and the machining tool can be moved three-dimensionally relative to one another. At least some of the slides may be movable under the control of a computer. The slides may be linear slides and or pivots. In a preferred embodiment the machine unit within the machining chamber has at least three linear slides and at least two pivots that are movable in a numerically controlled manner. Thus the machine unit preferably provides positioning of the dental workpiece relative to the machining tool at a desired number of degrees of translational and/or rotational freedom.

In one embodiment the air connection comprises a filter for retaining the process-originated material. Preferably the air connection is adapted such that air flowing through the connection is forced to pass through the filter, rather than around it. Preferably the filter is adapted to retain particles (for example particles of the dental material) conveyed in the intake air. The filter may be a circular filter, and may have a filter area of about between 1 m$^2$ and 10 m$^2$, preferably about 6 m$^2$. The filter may further conform to dust class M according to EN 60335-2-69 ANNEX AA. The filter may be adapted for cleaning by reverse air flow, washing, or the like. The filter may also comprise a cyclone filter, a liquid (for example oil) filter, and/or an electrostatic precipitator, for example. With respect to the air flow through the air connection during operation of the system the filter is preferably arranged downstream of the machining chamber, but upstream of the control unit.

In one embodiment the ventilation device is adapted to reduce an inner pressure in the machining chamber relative to an external pressure outside the machining chamber. In this case the air may be sucked from the machining chamber into the air connection. The ventilation device may further be adapted to increase the inner pressure in the machining chamber relative to an external pressure outside the machining chamber so that the air is pushed from the machining chamber into the air connection. Accordingly the ventilation device may include a vacuum source, or a compressor to create a source of higher-pressure air, or the equivalents of either or both.

The ventilation device may force air in the air connection towards the outlet, and cause further air to flow into the inlet. The ventilation device may be arranged adjacent the inlet of the air connection, adjacent the outlet of the air connection, and/or between the inlet and the outlet. The ventilation device is preferably arranged such that the air to the ventilation device is filtered by the filter. This is advantageous to reduce noise and wear of the ventilation device. The ventilation device may be provided by a suction device or a vacuum cleaner. A suitable industrial vacuum cleaner is for example available from Ziehl-Abegg AG, Germany under the designation RH25M-2DK.

In a further embodiment the control unit has a housing which comprises electronic circuitry. The electronic circuitry is preferably adapted to control the operation of components of the machine unit, for example to control the operation of motors, evaluate the output of sensors and/or to execute program commands. In a preferred embodiment the electronic circuitry comprises at least one microprocessor. The housing is preferably further adapted to be passed through by the air. Thus the control unit, particularly the electronic circuitry, may be ventilated by the air. The air may therefore be used to cool the control unit and the electronic circuitry therein. As an advantage the control unit may be reliably kept on a certain temperature, or kept below a certain maximum temperature, during operation of the machine. Further a separate ventilation device especially for ventilating the control unit, to be used with a corresponding separate filter, may be dispensable. Further thermostats in the control unit may be dispensable because flow rates as typically used for discharging process-originated material may effectively ventilate the control unit within a wide range of operational conditions of the system.

In one embodiment the control unit has a heat sink which is thermally connected to at least one element of the electronic circuitry of the control unit. The heat sink may be arranged in the system of the invention to cooperate with the air connection, whereas the electronic circuitry itself is enclosed relative to the air connection. Thus the heat sink may be ventilated by the air, for example to cool the heat sink by forced thermal convection, and consequently the element that is thermally connected to the heat sink may be cooled by thermal conduction. The control unit may thus be reliably kept at or below a certain temperature during machine operation, and further contamination of the electronic circuit with particles may be prevented, for example in case of deficiencies in the air filtering.

Preferably in operation of the system an overall air flow is established with air flowing into the system and the air exiting the system. The air may enter the system and flow into the machining chamber of the machine unit. From the machining chamber the air (eventually loaded with material particles) may flow towards the filter (where the material particles are retained), and from the filter towards the control unit. From the control unit the air may exit the system again. The air during the overall flow through the system preferably gets filtered. Thereby particles may be captured structurally, or electrostatically, or in any other suitable way. Therefore a system according to the invention, operated in a dental lab, may also filter the ambient air in the lab. The air in a dental lab may be loaded with particles because a variety of materials are handled there, such as plastic or ceramic materials. The present invention may thus advantageously contribute to cleaning the ambient air in the dental lab. This may reduce or even eliminate the necessity of providing separate room air filtration devices or systems.

A second aspect of the invention relates to a use of air emitted from a suction unit for discharging a process-originated material, to cool a control unit. The control unit is preferably adapted for operation of a machine unit for processing a dental material to form a dental restoration. The air emitted from the suction unit is preferably obtained from filtering the air sucked into the suction unit. As an advantage the suction unit may have a double function. First, the suction unit may be used to discharge the process-originated material (such as waste, by-products, tool particles, or dust, for example) from a machine for making a dental restoration.

Further, the same suction unit may be used to cool the control unit of such a machine. Thus relatively powerful and reliable cooling of the control unit may be provided.

A third aspect of the invention relates to a method of ventilating a control unit which is adapted for controlling the operation of a machine unit for processing a dental material to form a dental workpiece. The method comprises the steps of:

discharging a process-originated material entrained by air; and guiding the air towards the control unit.

In one embodiment the air is used for discharging the process-originated material, and subsequently that air is guided towards the control unit. In another embodiment, however, the air is first guided towards the control unit, and subsequently used for discharging the process-originated material. Consequently the system of the invention may also be adapted to provide both options.

The step of guiding the air towards the control unit preferably comprises causing thermal interaction between the air and at least one element of electronic circuitry comprised in the control unit. The thermal interaction may include thermal convection between the air and the element, or thermal convection between the air and a heat sink that is thermally connected to the element.

In one embodiment the method comprises the step of filtering the air prior to guiding it into or past the control unit. The method of the invention may further comprise the step of providing an air connection between the machine unit and the control unit. The air connection may particularly be provided between a machining chamber of the machine unit and the control unit.

The method of the invention is advantageous in that it provides for a use of the same air for discharging the process-originated material, and to ventilate the control unit. Thus energy for additionally ventilating the control unit, and potentially even ventilating the room in which the unit is located, may be saved.

DETAILED DESCRIPTION OF THE INVENTION

Figure 1:
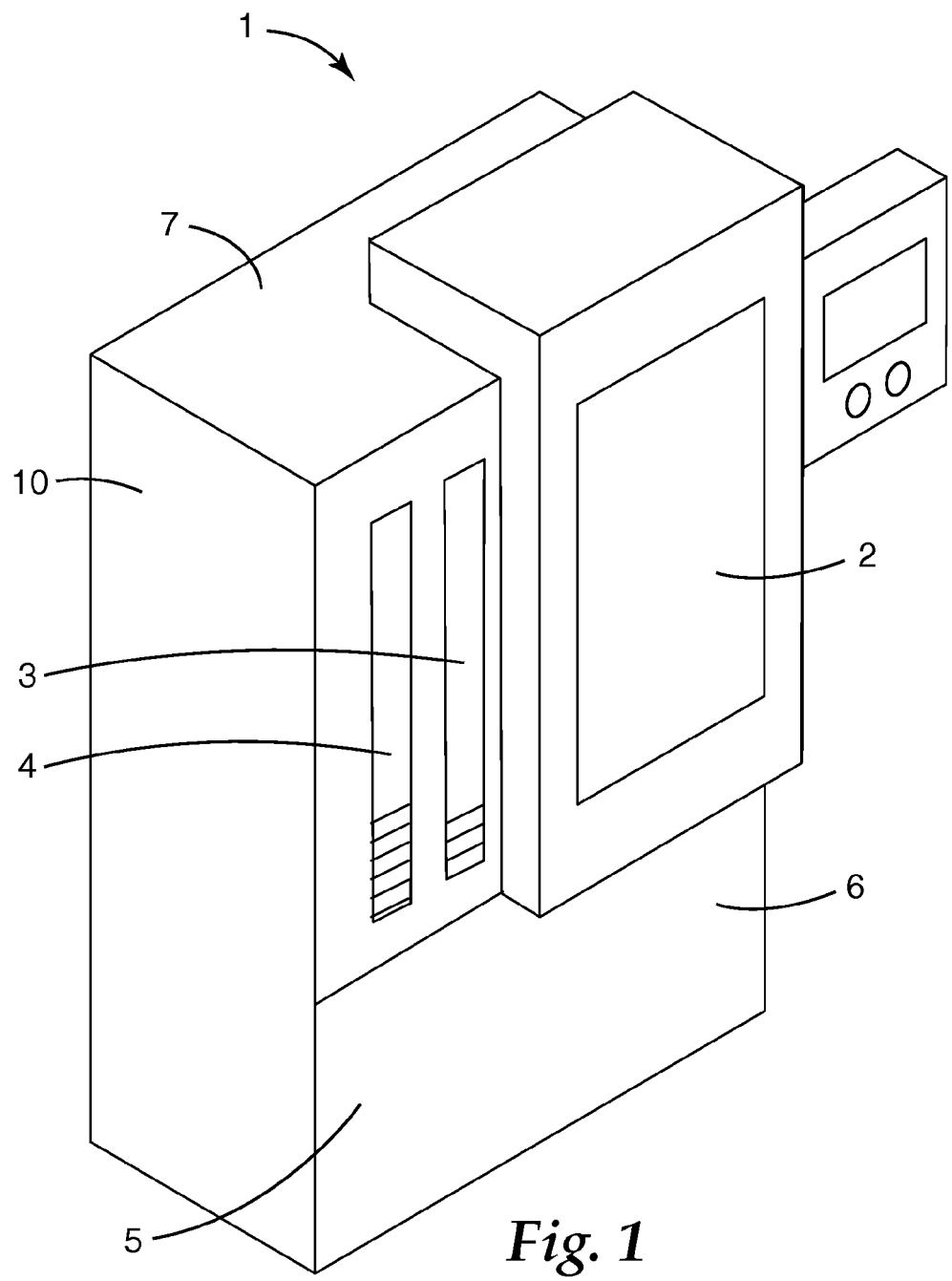
FIG. 1 is a perspective view of a system for making a dental restoration according to an embodiment of the invention.

FIG. 1 shows a system 1 for making a dental restoration. The system 1 has a body 10 in which a machine unit 7, and a control unit 5 are contained. The machine unit 7 and the control unit 5 are connected by an air channel (shown in FIG. 2). The machine unit 7 has a machining chamber 2 in which dental restorations can be machined. In the example the system 1 is a dental milling machine which is adapted to mill dental restorations from blanks of ceramic material. The dental workpieces are supplied to the system via an input magazine 3 in which multiple workpieces may be held and made available for successive machining in the machining chamber. Finished dental workpieces are preferably automatically placed in an output magazine 4 which typically also provides capacity for multiple finished dental workpieces. The dental workpieces are fixed in support frames that are shaped appropriately for automatic handling in the machine and for precise positioning in the machining chamber. A support frame for holding a dental workpiece as it may be used with the present invention is for example disclosed in patent application WO2008/097874.

A ventilation device 6 (shown in FIG. 2) is used to evacuate the machining chamber 2 so that chips, dust or other particles or gases originating from machining of the dental workpieces are continuously discharged (for example sucked away) from the machining chamber 2. This allows for example for continuous operation over a relatively long time because interruptions for manually disposing of process-originated waste may be prevented. The control unit 5 is preferably configured to control the operation of the system, particularly for controlling the operation of the machine unit 7. The control unit 5 in the example has electronic circuitry to drive servo-motors of the machine. The servo-motors drive and position slides and/or pivots of the machine. Such slides and pivots are adapted and arranged with respect to one another to position the workpiece and a machining tool (in this case a milling tool) three-dimensionally relative to one another during machining of a workpiece. A servo-motor may also be used to drive a spindle for rotating the milling tool. Further the control unit 5 may be adapted to run computer software, like an operation system as well as a user specific program. Such user specific program may, for example, comprise commands that are interpreted to control the machine operation to achieve a desired shape of the dental workpiece.

Figure 2:
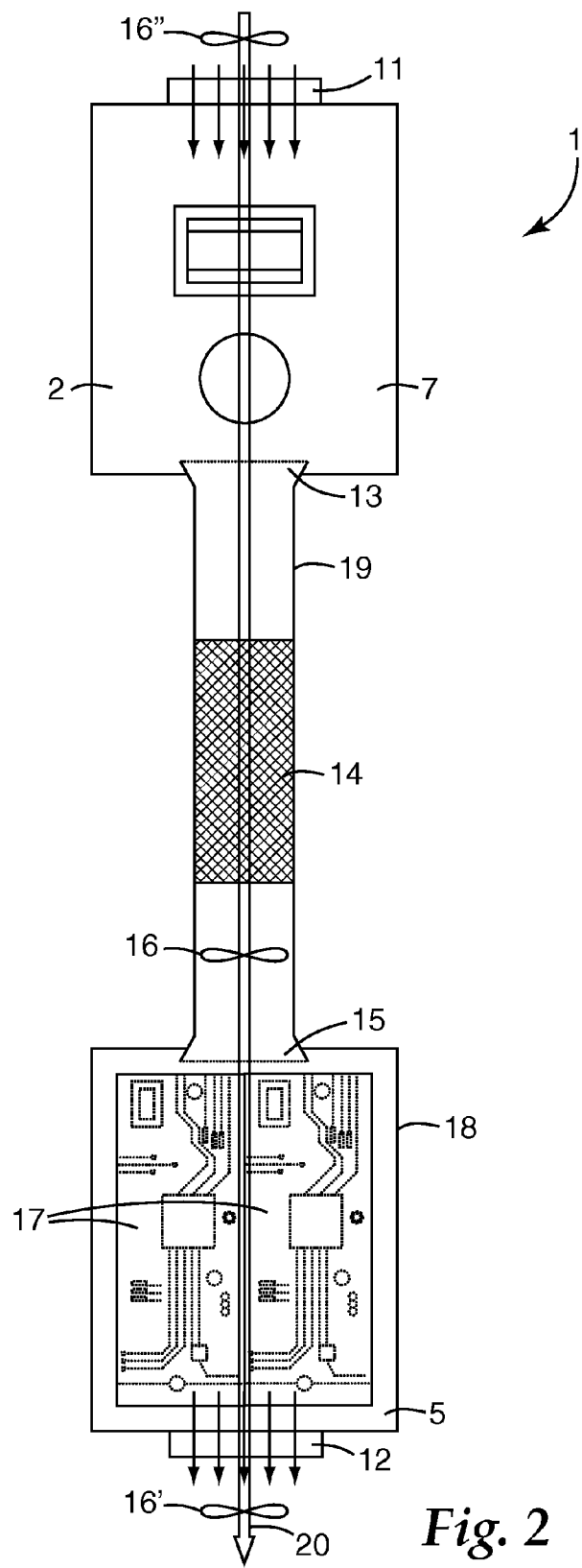
FIG. 2 is a schematic block diagram of a system for making a dental restoration according to an embodiment of the invention.

FIG. 2 is a block diagram of the system 1 illustrating the function of the system 1 in more detail. An air channel 19 provides air connection between the machine unit 7 and the control unit 5, in particular the air channel 19 may provide an air connection from the machine unit 7 toward the control unit 5. The air channel is illustrated as a pipe, but may be implemented in a variety of different forms, such as one or more pipes, hoses, openings, and combinations thereof. Further the system 1 has a supply opening 11 allowing air to penetrate from outside into the system 1 via the machining chamber 2, and an exit opening 12 allowing air to escape from the system 1 to the outside via the control unit 5. Thus an overall air flow path 20 is provided in the system between the supply opening 11 and the exit opening 12. The openings 11, 12 are indicated as discrete openings for better understanding only. Such openings may however be implemented in various different forms, for example in the form of multiple openings in the body of the system. Particularly the inlet opening 11 may be dispensable in case the machining chamber is not hermetically or tightly sealed. This may be the case for example if the machining chamber has a door which openably closes the machining chamber, but which does not have seals to hermetically seal the machining chamber.

In the illustrated embodiment, the air channel 19 has an inlet 13 and an outlet 15. The air channel 19 has a ventilation device 16 which forces air to flow along flow path 20, in particular forces air to flow towards the outlet 15 so that further air is drawn into inlet 13. The ventilation device 16 may also be arranged at other places, for example adjacent the exit opening 12, adjacent the supply opening 11 or at any other suitable place that allows air to be forced along flow path 20. Exemplary alternative or additional areas for the ventilation device 16 are indicated by elements 16' and 16". The air channel 19 further has a filter 14 which air flowing from the inlet 13 to the outlet 15 is required to pass. Air flowing along flow path 20, and particularly flowing in the air channel 19, thus is filtered. Therefore process-originated material, such as chips and/or dust, eventually entrained in the air may be retained in the filter. The control unit 5 preferably encapsulates the electronic circuitry 17 within a housing 18. The housing 18, the outlet 15 and the exit opening 12 are preferably adapted and arranged with respect to one another such that the air which flows from the outlet 15 toward the exit opening 12 is guided over the electronic circuitry 17. Therefore a thermal exchange between the electronic circuitry 17 and the air may be provided, so that for example heat which is generated in the electronic circuitry 17 may be dissipated from the control unit. In the example the control unit 5 is only ventilated by the air flow 20. Therefore an additional ventilation of the control unit is not necessary as it is typically present in prior art. As an advantage in this way the control unit may only be passed through by filtered air. Further a separate filter that may be required for separate ventilation can be saved.

Advantageously a ventilation device as it may be used with the present invention is adapted to generate an air flow that is strong enough to entrain the process-originated material (chips or dust). Such a ventilation device further may provide relatively high air flow rates, for example in a range of 600 m$^3$/h to 1000 m$^3$/h, and preferably about 800 m$^3$/h. The flow speed of the air in the vicinity of the inlet 13 or in the inlet 13 may be in a range of about 4 m/s to about 8 m/s, and preferably at about 5.5 m/s. The air flow rates may be sufficient to ventilate, for example to cool, powerful components of the electronic circuitry (for example power amplifiers for controlling the servo-motors). Another advantage results from the fact that typically the filter retaining the process-originated material is frequently serviced for removing the material from the filter. Therefore the filter is typically held in a good condition so that the flow resistance is kept low and consequently also the air flow rate can be maintained on a relatively high level. The cross-sectional area of different portions of the flow path 20 may vary between the supply opening 11 and the exit opening 12 (larger or smaller) so that the air velocity through those portions is increased or decreased. For example, the velocity in the vicinity of the workpiece may be relatively high to provide for entrainment of the process-originated material. Also in the vicinity of the circuitry the velocity may be high to provide for a good heat transfer. However in the area of the supply openings and or exit openings a larger cross-sectional area may provide for a lower velocity, for example to avoid noise. With increasing air flow rates the flow resistance of the filter may cause increasing back pressure in the upstream flow path. Therefore also in the area of the filter a lower velocity of the air may be preferred to prevent the filter from causing undesirably high back pressure. This can also be achieved by a widened cross-section of the flow path in the filter area.

The filter 14 and the ventilation device 16 may be arranged in an external unit which is connected to the machine unit 7 and the control unit 5. In one example the filter and the ventilation device may be parts of a commercially available industrial vacuum cleaner.

Dental Materials

Dental materials as they may be used with the present invention are for example dental ceramic materials or a dental glass-ceramic material. Such materials may be pre-sintered, or sintered.

The raw breaking resistance of the pre-sintered material or the facing precursor as referred to in this specification is preferably in a range of 10 to 15 MPa, more preferably in a range of 11 to 13 MPa, and preferably about 12 MPa according to the "punch on three ball test" as specified in ISO 6872.

The sintered material referred to in this specification preferably has a material density in a range of 2 g/cm$^3$ to 2.7 g/cm$^3$, and the pre-sintered material preferably has a material density in a range of 30% to 92% of the material density of the sintered material. Preferably the material density of the pre-sintered material is in a range of 40% to 60% of the material density of the sintered material, and more preferably in a range of 45% to 55%.

The raw breaking resistance of the sintered material as referred to in this specification is preferably in a range of 50 to 120 MPa, more preferably in a range of 68 to 74 MPa, and preferably about 72 MPa according to the "punch on three ball test" as specified in ISO 6872.

A ceramic material as referred to in this specification may be made of a pre-sintered or sintered material, for example a ceramic based on zirconium oxide. In particular the ceramic material may comprise between 90% and 99% by weight zirconium oxide, and preferably 91% to 97.25% by weight zirconium oxide. The ceramic material of the frame may further comprise 0%-1% by weight aluminum oxide. The ceramic material of the frame may also be based on aluminum oxide, meaning the ceramic material may comprise 90% to 99% by weight aluminum oxide and 0% to 1% by weight zirconium oxide. Further the ceramic material of the frame may comprise 0%-10% by weight of at least one of hafnium oxide, yttrium oxide and oxides from gallium, germanium, and indium. The ceramic material of the frame may also comprise 0.0005% to 1.5% by weight of coloring additives, selected from the group consisting of the oxides $Fe_2O_3$, $Er_2O_3$ and/or $MnO_2$. The ceramic material is preferably selected to be compatible for use in human bodies.

The glass-ceramic material as referred to in this specification is preferably selected to be compatible for use in human bodies. Typical glass ceramic materials are high-strength oxides of the elements of the main groups II, III and IV and the subgroups III and IV as well as their mixtures, in particular aluminum oxide, zirconium oxide, both partly and also fully stabilized, magnesium oxide, titanium oxide and mixtures of aluminum oxide, zirconium oxide, magnesium oxide and titanium oxide. An exemplary formulation of a glass ceramic as it may be used with the present invention comprises 60% to 70% by weight of silica, 9% to 13% by weight of alumina, 5% to 10% by weight of potassium-oxide, 9% to 13% by weight of sodium-oxide, 0% to 1% by weight of lithium-oxide, 2% to 5% by weight of calcium, 1% to 2% by weight of barium-oxide, 0% to 1% by weight of zirconium oxide and 0% to 1% cerium-oxide or cerium-fluoride.

Other materials may also be used, such as dental metals or alloys, and/or dental composites, as appropriate to form at least part of a dental restoration.

It will be appreciated that the embodiment shown in the Figures is just one example of how a system in accordance with the invention can be employed. However other embodiments providing equivalent effects are possible. In particular the arrangement of components relative to each other may be changed, or equivalent components may be used instead or in addition to the components described. Further, a single component may be implemented by two or more of the same or equivalent components. For example, it may be possible to implement an air connection between the machine unit and the control unit by two or more air channels which for example extend parallel, or two or more machine units may be connected to a single control unit, for example.

The invention claimed is:
1. A system for making a dental restoration comprising,
a machine unit for processing a dental material to form the dental restoration,
a control unit for controlling the operation of the machine unit, and
an air connection between the machine unit and the control unit, wherein the machine unit is adapted to mill or grind the dental material, wherein the machine unit is adapted to generate process-originated material, wherein the system is adapted to generate a flow of air for entraining the process-originated material in the air, and wherein the system is adapted to guide the air towards the control unit.

2. The system of claim 1, wherein the air connection has an inlet connected with the machine unit for receiving air from the machine unit and an outlet connected with the control unit for emitting the air towards the control unit.

3. The system of claim 2, being connectable or connected to a ventilation device which is adapted to generate an air flow in the air connection, such that the air connection receives the air from the machine unit and emits the air towards the control unit.

4. The system of claim 1, wherein the air connection is established between a machining chamber of the machine unit and the control unit, wherein the machining chamber is adapted to contain the process.

5. The system of claim 1, wherein the air connection comprises a filter for retaining the process-originated material.

6. The system of claim 5, wherein the filter has a filter area of between about 1 m² to 10 m².

7. The system of claim 5, wherein the filter, comprising at least one of a cyclone and an electrostatic precipitator.

8. The system of claim 1, wherein the control unit has a housing which comprises electronic circuitry, and wherein the housing is adapted to be passed through by the air.

9. The system of claim 3, wherein the ventilation device has at least one of an exhaust fan, and a compressor.

10. The system of claim 9, wherein the ventilation device is a suction device.

11. The system of claim 1, being adapted to machine a dental ceramic or dental glass-ceramic material.

12. The system of claim 1, being adapted to mill or grind a dental ceramic or dental glass-ceramic material.

13. The system of claim 5, wherein the filter is downstream of the machining chamber, but upstream of the control unit.

14. A method of ventilating a control unit, wherein the control unit is adapted to control the operation of a machine unit for processing a dental material to form a dental workpiece, wherein the machine unit is adapted to mill or grind the dental material, wherein the machine unit is adapted to generate process-originated material, wherein the method comprises:

entraining process-originated material in air; and guiding the air into the control unit.

15. The method of claim 14, comprising the step of filtering the air prior to guiding it into the control unit.

* * * * *